United States Patent [19]

Rösinger et al.

[11] 3,948,742
[45] Apr. 6, 1976

[54] PREPARATION OF POLYCHLORCYCLOPENTANE AND HEXACHLORCYCLOPENTADIENE

[75] Inventors: Sigurd Rösinger, Frankfurt am Main; Heinz Boesenberg; Adolf Gaube, both of Hofheim, Taunus, all of Germany

[73] Assignee: Hoechst Aktiengesellschaft, Frankfurt am Main, Germany

[22] Filed: Dec. 16, 1971

[21] Appl. No.: 208,871

[30] Foreign Application Priority Data
Dec. 19, 1970 Germany............................ 2062773

[52] U.S. Cl............................................ 204/163 HE
[51] Int. Cl.$^2$...................... B01D 1/10; C07C 17/10
[58] Field of Search.............................. 204/163 HE

[56] References Cited
UNITED STATES PATENTS
2,473,162   6/1949   McBee et al.................... 204/163 R
FOREIGN PATENTS OR APPLICATIONS
1,055,410   1/1967   United Kingdom.......... 204/163 HE Primary Examiner—Benjamin R. Padgett
Assistant Examiner—E. A. Miller
Attorney, Agent, or Firm—Curtis, Morris & Safford

[57] ABSTRACT

Polychlorcyclopentane and hexachlorcyclopentadiene are prepared by reacting liquid chlorinated cyclopentane with gaseous chlorine in the presence of an electromagnetic radiation and optionally by a subsequent reaction of these higher chlorinated cyclopentanes with chlorine at a temperature of more than 300°C to yield hexachlorcyclopentadiene.

6 Claims, 2 Drawing Figures

PREPARATION OF POLYCHLORCYCLOPENTANE AND HEXACHLORCYCLOPENTADIENE

The present invention relates to a process for the preparation of polychlorcyclopentane and hexachlorcyclopentadiene.

Polychlorcyclopentane (PCP) is an intermediate product for the preparation of hexachlorcyclopentadiene (HCP) which serves for the preparation of insecticides and fungicides as well as of plasticizers, and which makes certain polymers and epoxide resins flame resistant.

A summary of the preparation of PCP and HCP is given by F. Runge, H. Bendix and H. Breuer: "Über die Technologie und Chemie des Hexachlorcyclopentadiens" in "Chemische Technik" 16 (1964), pages 203 to 208. In this publication, a description is also given of processes, in which hyrdocarbons containing 5 carbon atoms are chlorinated by an irradiation with visible and ultra-violet light (see also U.S. Pat. No. 2,473,162).

The present invention provides a process for the preparation of polychlorcyclopentane and hexachlorcyclopentadiene by reacting liquid chlorinated cyclopentanes with gaseous chlorine and, optionally, by a subsequent reaction of these higher chlorinated cyclopentanes with chlorine at a temperature of more than 300°C to yield hexachlorcyclopentadiene, which comprises reacting chlorinated cyclopentanes having a chlorine content of about 4 chlorine atoms per molecule with gaseous chlorine at a temperature of from 40° to 170°C, preferably from 80° to 135°C, and at a pressure of from 0 to 20 atmospheres gage, in the presence of an electro-magnetic radiation with a wave length of less than 1 A, and with a dose rate of from $10^2$ to $10^7$ rad per hour, to form polychlorcyclopentanes having a chlorine content of from 5.0 to 7.0, preferably from 5.8 to 6.2 chlorine atoms per molecule and, optionally, reacting the intermediate product thus obtained subsequently in the gaseous phase with chlorine to give hexachlorcyclopentadiene.

The cyclopentanes used according to the process of the invention which have a chlorine content of about 4 chlorine atoms per molecule are obtained by way of chlorination of cyclopentadiene at a temperature of from 20° to 60°C (cf. F. Runge et al. loc. cit, page 204).

The speed of the reaction of the process according to the invention depends on the amount of chlorine introduced. An amount of chlorine exceeding the stoichiometrical ratio is advantageously used. Satisfactory results are already obtained, if there is a minor molar excess of chlorine, for example, 0.1 or 0.2 mole in excess of the chlorinated cyclopentane; higher excess amounts of chlorine further increase the yield. It can therefore be advantageous to choose the excess amount of chlorine for this reaction, which proceeds rather slowly, in a very high range, and then to guide the chlorine-containing exhaust gas into a further reaction stage. It may also be advantageous to circulate the chlorine by means of a pump.

The reaction temperature and, as a consequence, the residence time are of great importance in the process of chlorination under the action of radiation according to the invention.

Low temperatures require a long reaction time, until the tetrachlorcyclopentane has been completely chlorinated to give polychlorcyclopentane having an average chlorine content of from 5.0 to 7 chlorine atoms, whereas temperatures that are too high result in a discoloration of the product.

The temperatures which are most advantageous for the process of the invention are therefore in the range of from 40° to 170°C, preferably between 80° and 135°C. If the high energy electro-magnetic wave radiation is used according to the invention, however, the necessary residence time of the liquid in the reaction zone is considerably shorter than in the case of know processes, so that discolorations of the product are avoided even in the higher range of the temperature limits indicated above. Depending on the residence time, a reaction product is obtained according to the invention, which contains from 5.0 to 7 chlorine atoms per molecule. The chlorination is preferably carried out to an extent that from 5.8 to 6.2 chlorine atoms per molecule are taken up, since a product of this kind has the most favourable properties for the subsequent reaction to form hexachlorcyclopentadiene.

The radiation chlorination in accordance with the invention may be carried out at normal pressure or at an elevated pressure. An increase of the pressure up to 20 atmospheres gage does not effect a variation of the composition and the properties of the polychlorcyclopentane. It is advantageous that the speed of the reaction increases in proportion to the chlorine pressure, so that smaller and more profitable installations can be used. The use of moderate pressures within the range of from 0.5 to 5 atmospheres gage is preferred.

The chlorination according to the invention is effected in the presence of an electro-magnetic radiation with a wave length of less than 1 A, and with a dose rate of from $10^2$ to $10^7$ rad per hour. This radiation can be produced by means of machines, for example, X-ray apparatus or accelerators or in a nuclear reactor. It may also originate from radionuclides, for example, Co-60 or Cs-137. Within the indicated limits, a higher dose rate results in an increase of the rate of reaction, and thus a reduced residence time of the irradiated liquid in the reaction vessel.

Figure 1:
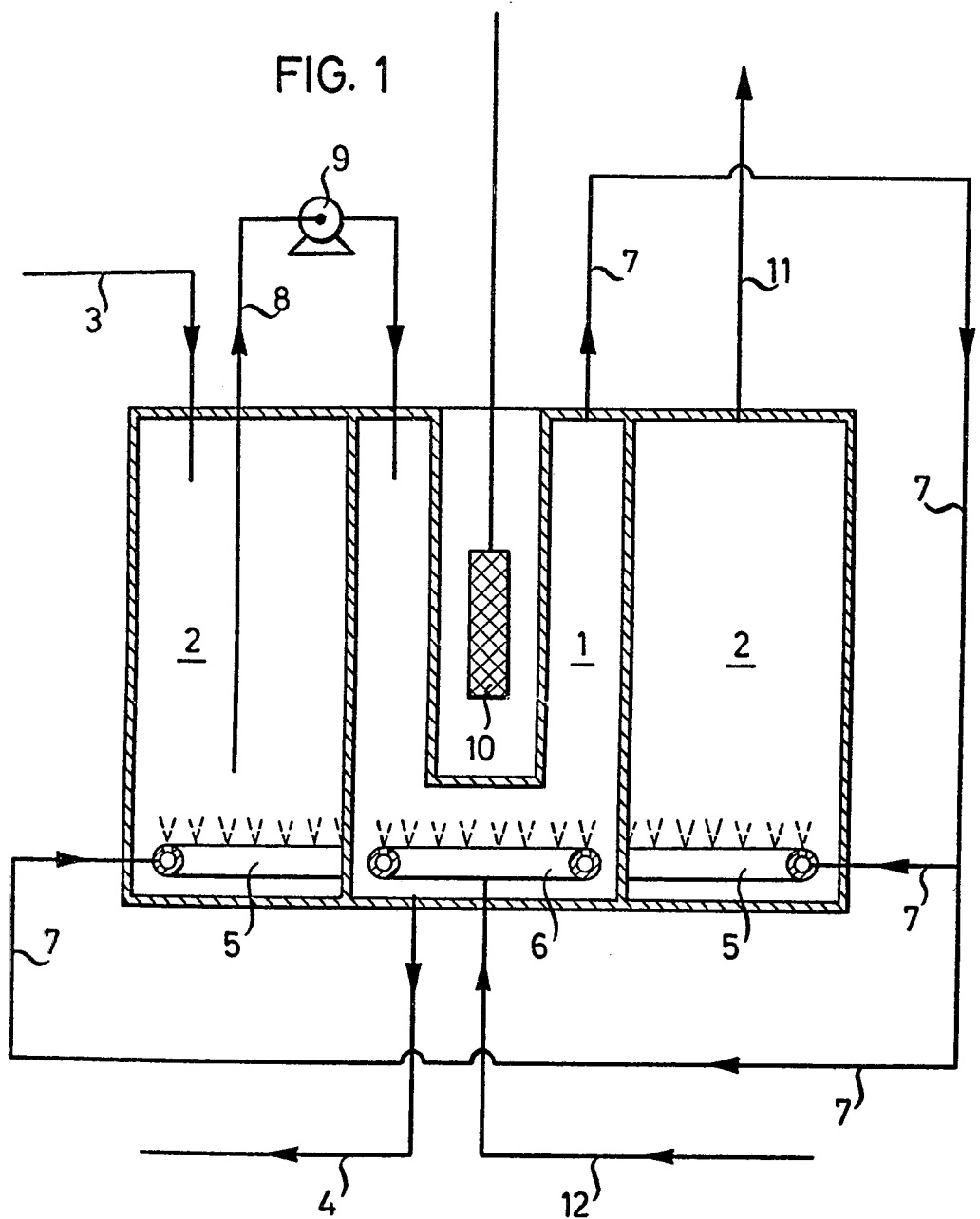
FIG. 1 shows a radiation chlorination apparatus including a double walled reactor.

The rate of chlorination by radiation further depends on the degree of chlorination of the cyclopentane. With a chlorine content of the cyclopentane of up to about 5 chlorine atoms per molecule, the rate of chlorination is higher than with a higher chlorine content. It is therefore possible to perform the chlorination at first with a minor dose rate. In order to obtain an absorption of energy as high as possible under these conditions, it is advantageous to carry out the reaction in a double-walled reaction vessel, in which the source of radiation is located within a central tube. An arrangement of this kind is shown in FIG. 1 attached. Within the inner part 1 of the vessel, the radiation is applied with a considerably higher dose rate than in the outer part of the vessel, thus increasing the rate of chlorination accordingly.

In an installation according to FIG. 1, the tetrachlorcyclopentane coming from the first chlorination stage is pumped via conduit 3 into the outer reaction zone 2 of the double-walled reaction vessel, and is there reacted with chlorine, which is admitted via conduit 7 and gas ring 5, until an average chlorine content of about 5 chlorine atoms per molecule is reached. This product is pumped via conduit 8 and pump 9 into the inner part 1 of the reactor, where it is reacted with chlorine coming from conduit 12 and gas ring 6 to give polychlorcyclopentane having an average chlorine content of 6 chlorine atoms per molecule. The source of radiation 10 is located in the center of the reaction vessel. The polychlorcyclopentane is then fed via conduit 4 into the high temperature stage for further chlorination. The exhaust gas containing hydrogen chloride and chlorine is eliminated via pipe 11 from the reaction vessel.

The double-walled reaction vessel and the countercurrent gassing has the advantage that the slower reaction in the inner part of the vessel is increased in the presence of a larger amount of chlorine, the space-time yield thus being influenced in a particularly favourable way. In the double-walled reaction vessel with a central source of radiation, a homogeneously chlorinated polychlorcyclopentane is obtained, which does not contain any proportion of insufficiently chlorinated compounds. For static reasons it is necessary that the reaction vessels should have a minimum wall thickness which is already sufficient for reactions carried out under a moderate pressure. Therefore, no additional costs for the apparatus are involved in the case of a pressure reaction under the said conditions. On the other hand, the installation can be laid out in a smaller scale, as the space-time yield can be increased both by an increase in pressure and by the gas guidance described above.

The advantages of the process of the invention as compared against the known process of chlorination using ultra-violet light are the following.

The ultra-violet light is already absorbed in the first few millimeters of the solution, i.e. no light can penetrate even into parts of the reaction vessel located at a short distance from the source of radiation, so that no reaction can develop in these places. This difficulty may be overcome in a way that either a large number of UV lamps are installed in the reaction vessel, or the liquid has to be stirred or pumped at great speed, in order to transport each volume element of the reaction mixture at least once through the radiation zone. In contradistinction thereto, the reaction takes place within the total volume of the reaction mixture, if X-rays or gamma rays are used.

Another disadvantage of the known chlorination process by means of UV light is the fact that coloured deposits are frequently formed on the protecting quartz tubes of the UV lamps, which deposits reduce the penetration of the light and finally prevent it. Since the tetrachlorcyclopentane used as starting material in the radiation chlorination according to the invention shows in most cases a more or less strong colouration, it allows only a fraction of the UV light to become active for the chlorination; this is why the yield of the process is reduced in a way that cannot be foreseen. This is particularly disadvantageous in the case of a continuous performance of the process with a subsequent reaction of the polychlorcyclopentane at a high temperature to yield hexachlorcyclopentadiene, since the second step of the reaction strongly depends upon the constant feed of polychlorcyclopentane. These disadvantages are avoided, if X-rays or gamma rays are used, since there are no materials that cannot be penetrated by these types of rays.

Another advantage of the use of X-rays or gamma rays as compared against the use of the UV radiation can be seen in the fact that reactions may be carried out at an elevated pressure, as this type of radiation is hardly diminished by pressure-proof walls of the reaction vessels, which are made of nickle, for example. The protecting quartz tubes, which are required for UV lamps, however, are not very stable, but brittle; they cannot be used, therefore, in processes being performed under pressure.

Another advantage of the process according to the invention is the low need of repair of the preferred source of gamma radiation, as compared against the use of numerous UV lamps with the necessary electric installation. In this connection, for example, the strong corrosion on the electric wiring has to be taken into consideration, as well as the fact that UV lamps have to be exchanged after a relatively short time, since their light emission decreases with an increasing time of operation. Besides, there is also a constant consumption of electric energy. In contradistinction thereto, the operating costs are very small, if radiation from radionuclides is used. This is true in particular, if radionuclides are used, which have a very long half-life, for example, caesium-137 having a half-life of 30 years. During a time of several years, the radiation rate of such a source is practically constant.

In the following examples the refraction valve is used in order to determine the chlorine content of the liquids used. For this purpose the connection between the refraction valve and the chlorine content is determined empirically. The chlorine content of the liquid is measured by means of the elementary analysis. Thus, the refraction value may be used for determining the degree of chlorination in the case of the discontinuous operation, as well as for the process control in the case of the continuous operation.

The following Examples serve to illustrate the invention.

EXAMPLE 1

208.6 g of a chlorinated cyclopentane having an average chlorine content of 4 chlorine atoms per molecule (which corresponds to 1 mole of tetrachlorcyclopentane were introduced into a cylindrical reaction vessel having a capacity of 250 milliliters and being provided with a gas inlet frit, the vessel being connected with a reflux condenser. The liquid was maintained at 135°C, and chlorine gas was introduced in an amount of 51.1 g per hour. After the reaction mixture had been saturated with chlorine, it was exposed, at the same temperature, to a cobalt-60 gamma radiation with a dose rate of $3.5 \cdot 10^5$ rad per hour. The progress of the reaction was observed by controlling the weight increase. After 4.1 hours, the radiation and the gas supply were interrupted. After having been irradiated with a total dose of 1.4 Mrad, the liquid having a refraction value of $n_D^{20} = 1.5470$ had taken up 71.1 g of chlorine. The chlorine content of the liquid obtained was 6.1 chlorine atoms per molecule. The opaque dark brown starting product used for the reaction was converted quantitatively, by way of the radiation reaction, into a light yellow transparent liquid having an average chlorine content of 6.1 chlorine atoms per molecule of cyclopentane.

Of the 279 g of liquid obtained, part was converted into the gaseous phase at 350°C, and was subsequently reacted quantitatively with three times the molar amount of chlorine at 450°C, in a reaction vessel made of nickel. The raw product thus obtained was analysed by means of the gas-liquid distribution chromatography; it contained 96.5 % of hexachlorcyclopentadiene.

EXAMPLE 2

208 g each of the starting product used in Example 1 were introduced into the apparatus described above. Subsequently, chlorine gas was introduced at atmospheric pressure in an amount of 70 g per hour, with a dose rate of $1 \cdot 10^4$ rad per hour. Under these conditions the reaction was continued at different temperatures for such a time, until the product had taken up the desired number of 6 chlorine atoms per molecule; its refraction value was then $n_D^{20} = 1.5461 \mp 0.0004$.

At a temperature of 150°C, 7 hours were required, at 135°C, 9 hours, and at 100°C, 12 hours, until the reaction was completed, which was determined by means of a refractometer. At a reaction temperature of 50°C, the time required to complete the reaction is more than 20 hours. The liquid obtained was converted into hexachlorocyclopentadiene, as has been described in Example 1.

EXAMPLE 3

310 g each of a chlorinated cyclopentane having an average chlorine content of 4 chlorine atoms per molecule was introduced into a pressure apparatus having a capacity of 500 milliliters, and being provided with a gas inlet tube and a reflux condenser; subsequently the cyclopentane was reacted at 100°C with a dose rate of $2 \cdot 10^5$ rad per hour and a chlorine throughput of 70 g per hour.

The reaction was stopped after two hours and an absorption of a dose of 0.4 Mrad. After a reaction under a pressure of 1580 mm of mercury, a chlorinated product was obtained quantitatively, which had an average chlorine content of 6.1 chlorine atoms per molecule and showed a refraction value of $n_D^{20} = 1.5461$.

The liquid obtained could be converted into hexachlorocyclopentadiene, as has been described in Example 1.

EXAMPLE 4

Figure 2:
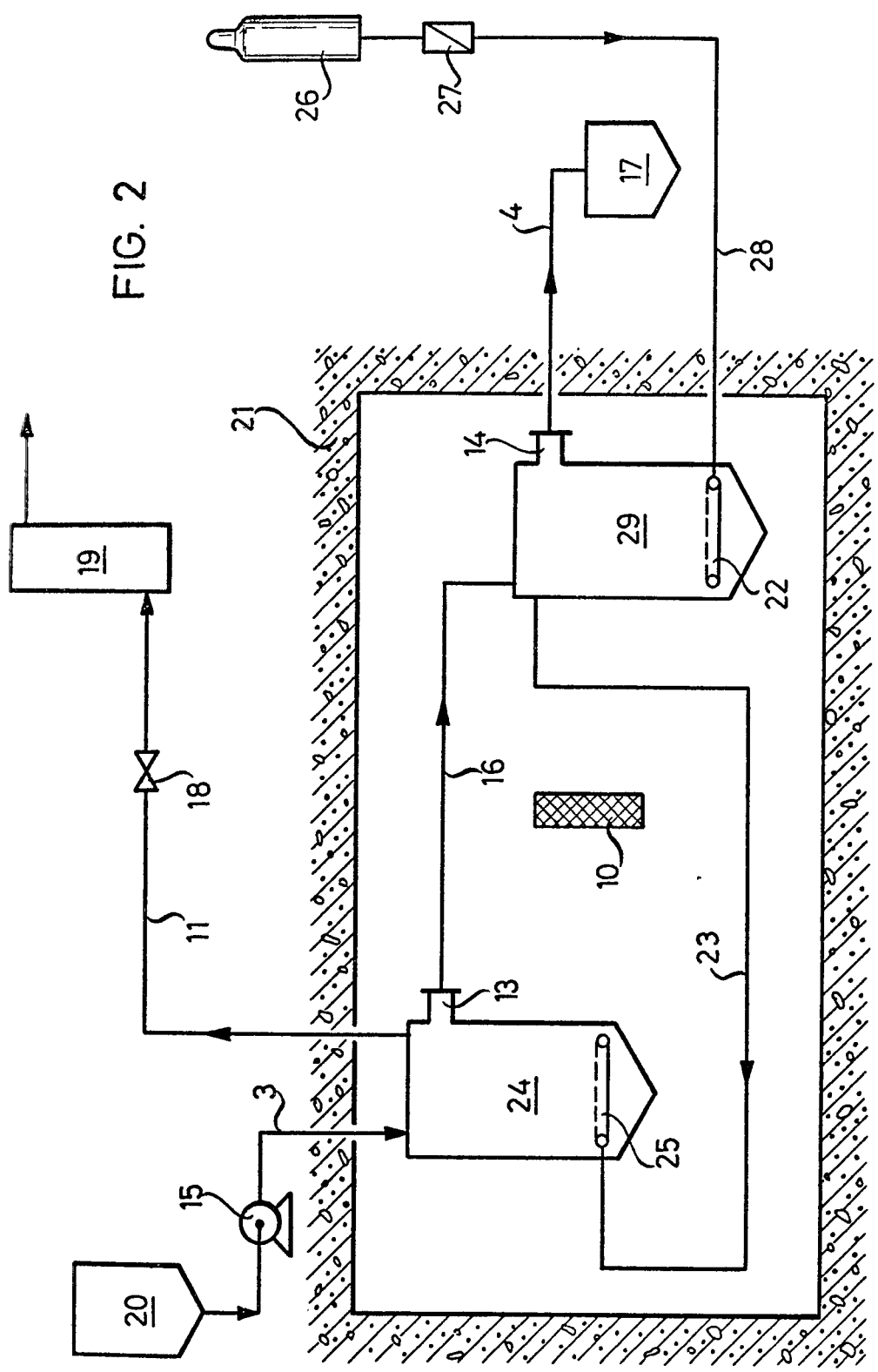
FIG. 2 shows a two stage radiation chlorination apparatus.

The chlorination of a chlorinated cyclopentane having a chlorine content of 4 chlorine atoms is carried out in an apparatus operated continuously. The installation shown in FIG. 2 corresponds to the performance of the reaction in a double-walled reaction vessel, as has been described before. The installation comprises two stages, it consists of two reactors 24 and 29, each having a contents of 16 parts by volume, which are provided in each case with an overflow 13, 14. At the bottom of the reactors there have been installed gassing devices 22, 25, through which the chlorine is blown into the liquid. The reactors have been filled with 15 parts by volume of chlorinated cyclopentane having an average chlorine content of 4 chlorine atoms per molecule in such a way that, if a further amount of starting material is pumped in, the same volume runs over via the overflow from reactor 24 and via conduit 16 into reactor 29, and from there via conduit 4 into receiving vessel 17. The starting material is pumped from supply vessel 20 via pump 15 and conduit 3 into reactor 24. The liquid which is chlorinated in this reactor flows via overlow 13 and conduit 16 into reactor 29. The cyclopentane chlorinated up to an average chlorine content of 6 chlorine atoms runs from reactor 29 via overflow 14 and conduit 4 into receiving vessel 17 for the final product. The gaseous chlorine is taken from gas bottles 26, its amount is measured in a rotameter 27, and it is then blown into reactor 29 via conduit 28 and gas ring 22 at first in counter current flow. The exhaust gas from reactor 29, which already contains HC1, is blown into reactor 24 in counter current via conduit 23 through gas ring 25; the exhaust gas is guided from the reactor via conduit 11 to a pressure control mechanism 18 and from there to exhaust gas washer 19. The radiation of the two reactors is effected by a source of 15,000 Curie cobalt-60 10 having a dose rate of $3 \cdot 10^4$ rad per hour in a radiation chamber screened by concrete 21. At the beginning of the process, the chlorination in reactor 24 is carried out to such an extent that the product has a refraction value of $n_D^{20} = 1.5360$. Besides, the chlorination in reactor 29 has to be effected to an extent that the refraction value of the chlorinated cyclopentane $n_D^{20} = 1.5460$, which corresponds to a chlorine content of 6 chlorine atoms per molecule of cyclopentane. After that the process can be carried out continuously by pumping the starting material at a constant speed of pumping via pump 15 and conduit 3 into reactor 24, from where the prechlorinated product flows over into reactor 29 via conduit 16, the chlorinated final product having an average chlorine content of 6 chlorine atoms per molecule of cyclopentane then runs from reactor 29 via conduit 4 into receiving vessel 17.

At a chlorine pressure of 1.0 atmosphere gage, which was measured at pressure control mechanism 18, 1.1 m³ of chlorine per hour is introduced via conduit 28 into reactor 29. The exhaust gas coming from reactor 29, which already contains a proportion of hydrogen chloride, is subsequently guided via conduit 23 into reactor 24, where its chlorine proportion further reacts with the liquid. The exhaust gas escaping from reactor 24 via conduit 11 consists mainly of gaseous hydrogen chloride containing chlorine; it is then guided to exhaust gas washer 19.

The dark-coloured starting material, the density of which is 1.49 g/cm³, is pumped in an amount of 4.2 liters per hour into reactor 24 by means of pump 15. Under the specified conditions, 8.5 kg per hour of a light yellow polychlorcyclopentane having an average chlorine content of 6 chlorine atoms per molecule flows from reactor 29 via conduit 4 into receiving vessel 17, when the process is carried out continuously. During the continuous operation, the refraction value of the liquid in reactor 24 is $n_D^{20} = 1.5360$, while the refraction value of the polychlorcyclopentane flowing off reactor 29 is $n_D^{20} = 1.5460$.

Part of the latter polychlorcyclopentane is converted continuously into the gaseous phase at 350°C, and is subsequently reacted quantitatively at 450°C with 3 times the molar amount of chlorine in a reaction vessel made of nickel. The raw product thus obtained is analysed by means of the gas-liquid-distribution chromatography; it contains 97 % of hexachlorcyclopentadiene.

What is claimed is:

1. A process for the preparation of polychlorcyclopentane by reacting liquid chlorinated cyclopentanes with gaseous chlorine, which comprises reacting chlorinated cyclopentanes having a chlorine content of about 4 chlorine atoms per molecule with gaseous chlorine at a temperature in the range of from 40° to 170°C, and at a pressure of from 0 to 20 atmospheres gage, in the presence of an electro-magnetic radiation with a wave length of less than 1 A, and with a dose rate of from $10^2$ to $10^7$ rad per hour, to form polychlorcyclopentanes having a chlorine content of from 5.0 to 7.0 chlorine atoms per molecule.

2. A process as claimed in claim 1, which comprises carrying out the reaction at a temperature of from 80° to 135°C.

3. A process as claimed in claim 1, wherein a polychlorcyclopentane having a chlorine content of from 5.8 to 6.2 chlorine atoms per molecule is obtained.

4. A process for the preparation of hexachlorcyclopentadiene by reacting liquid chlorinated cyclopentanes with gaseous chlorine, and subsequently reacting these higher chlorinated cyclopentanes with chlorine at a temperature of more than 300°C to yield hexachlorcyclopentadiene, which comprises reacting chlorinated cyclopentanes having a chlorine content of about 4 chlorine atoms per molecule with gaseous chlorine at a temperature of from 40° to 170°C, and at a pressure in the range of from 0 to 20 atmospheres gage, in the presence of electro-magnetic radiation with a wave length of less than 1 A, and with a dose rate of from $10^2$ to $10^7$ rad per hour, to form polychlorcyclopentane having a chlorine content of from 5.0 to 7.0 chlorine atoms per molecule, and reacting the intermediate product thus obtained subsequently in the gaseous phase with chlorine to yield hexachlorcyclopentadiene.

5. A process as claimed in claim 4, which comprises carrying out the reaction of polychlorcyclopentane with chlorine at a temperature in the range of from 80° to 135°C.

6. A process as claimed in claim 4, wherein a polychlorcyclopentane having a chlorine content of from 5.8 to 6.2 chlorine atoms per molecule is obtained.

* * * * *